United States Patent [19]

Schneider

[11] 4,224,179

[45] Sep. 23, 1980

[54] PROCESS FOR THE PREPARATION OF LIPOSOMES IN AQUEOUS SOLUTION

[75] Inventor: Michel Schneider, Geneva, Switzerland

[73] Assignee: Battelle Memorial Institute, Carouge-Geneva, Switzerland

[21] Appl. No.: 931,242

[22] Filed: Aug. 4, 1978

[30] Foreign Application Priority Data

Aug. 5, 1977 [CH] Switzerland .................... 9616/77

[51] Int. Cl.$^2$ ............................................. B01J 13/02
[52] U.S. Cl. ........................................ 252/316; 8/526; 8/584; 8/587; 252/312; 252/314; 252/317; 252/318; 252/522 R; 424/36; 424/94; 424/177; 424/199; 424/319; 424/180
[58] Field of Search ............... 260/208; 252/312, 313, 252/314, 315, 316, 317, 318

[56] References Cited

U.S. PATENT DOCUMENTS

| | | | |
|---|---|---|---|
| 3,361,680 | 1/1968 | Bohrer | 252/314 |
| 4,089,801 | 5/1978 | Schneider | 252/316 |

FOREIGN PATENT DOCUMENTS

| | | | |
|---|---|---|---|
| 861011 | 10/1977 | Belgium | 252/316 |
| 2532317 | 1/1976 | Fed. Rep. of Germany | 252/316 |
| 2347924 | 11/1977 | France | 252/316 |
| 7701554 | 8/1976 | Netherlands | 252/316 |
| 1502774 | 3/1978 | United Kingdom | 252/316 |

OTHER PUBLICATIONS

Tyrrell et al., Biochimica & Biophysica Acta, vol. 457, pp. 259–302, (1976).

*Primary Examiner*—Floyd D. Higel
*Attorney, Agent, or Firm*—Finnegan, Henderson, Farabow, Garrett & Dunner

[57] ABSTRACT

A process for the preparation of a solution or suspension of liposomes in an aqueous medium comprising the steps of dispersing a first aqueous liquid in an essentially water-insoluble solvent in the presence of a compound of the formula XY wherein X is a hydrophilic lipophobic group and Y is a lipophilic hydrophobic group to form a dispersion of liposome precursors in the solvent, the precursors consisting of small vesicles of the first aqueous liquid surrounded by a monomolecular film of compound XY, emulsifying the liposome precursors in a second aqueous medium in the presence of a compound of the formula ZW wherein Z is a hydrophilic group and W is a hydrophobic group to thereby form a solution or suspension of liposomes in the second aqueous medium, said liposomes consisting of the first aqueous liquid surrounded by a bimolecular film of the structure XY-WZ and removing the water-insoluble solvent prior to after said emulsification.

19 Claims, No Drawings

PROCESS FOR THE PREPARATION OF LIPOSOMES IN AQUEOUS SOLUTION

The present invention concerns a process for the preparation of solutions or suspension of liposomes in aqueous media.

Liposomes are microscopic vesicles, generally spherically shaped, formed from one or several concentric layers (lamellae) of lipid molecules, i.e. compounds having a lipophobic hydrophilic moiety and a lipophilic hydrophobic moiety. The lamellae of a water-soluble liposome are formed of at least one bimolecular lipid layer (which lipid can be represented hereinafter by the formula XY, wherein X is the hydrophilic moiety and Y is the hydrophobic moiety), the molecules of this layer being so oriented that the hydrophilic functions thereof stay in contact with the aqueous phase. Since the liposomes lamellae are being separated from each other by a water film, they have a wall-like structure which can be schematically represented, in section, by a series of molecular composites XY—YX stacked together in the plane of the paper. The size of the liposomes vesicles is extremely variable and depends, as will be described hereinafter, on the methods used for the manufacture thereof; in general, they have a 25 to 30,000 nm diameter and the lipid film around is about 3 to 10 nm. The smaller liposomes of this range in general have a monolamellar envelope, that is a monolayer of the following molecular association:

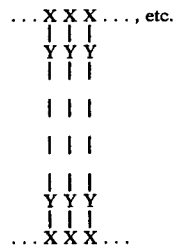

The aqueous phase in which the liposomes are in solution or suspension is generally different from the aqueous phase contained in the inside thereof. Hence, the preparation of liposomes constitutes a very practical encapsulation method for trapping an aqueous liquid and such vesicles are particularly useful for introducing biologically active substances into living organisms, namely drugs or medicines, while preventing an early degradation thereof (for instance by stomach or intestine fluids) before these substances have a chance to reach the specific organ to be cured. By a proper selection of the compound(s) alone or together with other surfactants ZW wherein Z has the same definition as X and W has the same definition as Y, XY to form the liposomes walls, it is effectively possible to form liposomes with walls resisting the action of specific categories of organic fluids and being dissolved only by the media which exist within the organs wherein the biologically active substances must be liberated. Consequently, in general, the liposomes contain within their inside an aqueous solution of the encapsulated product and, in order to constitute the liposome solution itself, they will be dissolved or dispersed in water or in any other aqueous phase, for instance in aqueous NaCl of isotonic concentration.

Acknowledgment is made to the fact that the content of the liposomes of the present invention is not limited to medicines, drugs and other biologically active compounds but covers other water-soluble materials. As such other materials, the followings can be recited: dyestuffs, perfumes, flavours or, in general, ingredients to be used within specific industrial processes or compositions of matter but which should be released with some delay relative to their initial addition, or used up progressively in the course of time. It would be therefore wrong to consider that liposomes are only pharmaceutical products per se, although they may, as mentioned above, be the vehicles for drugs or alike.

It will also be noted that the term "lipid" as used herein is taken in its widest sense, i.e. it comprises most compounds belonging to the definition XY or ZW given before, either natural or synthetic, such as, for instance, many kinds of surfactants used in the industries of pharmacy, cosmetics, textiles, detergents, foodstuffs, etc . . .

There exists already several methods for the preparation of liposomes solutions in the above defined sense, which methods are described in the following reference: "New Aspects of liposomes" by D. A. Tyrrell, T. D. Heath, C. M. Colley & B. E. Ryman, Biochimica & Biophysica Acta, 457 (1976), 259–302. One of these processes comprises heating a heterogeneous mixture of a lipid and the aqueous liquid to be encapsulated to a temperature above room temperature, then subjecting the mixture to violent agitation followed by sonication, that is, to vibrations of sonic or ultra-sonic frequencies.

Another method comprises dissolving a compound of formula XY (X and Y having the above defined meaning), e.g. a lipid, in a volatile solvent, evaporating said solution contained in a vessel thus forming a film of the lipid of the walls of the vessel, introducing the liquid to be encapsulated in the flask and, finally, subjecting the latter to sonic or ultra-sonic frequencies whereby part of said liquid will be divided into droplets surrounded by lipid envelopes. More prolonged is the treatment, more of the liposomes tend to acquire a mono-lamellar shell.

It is realized that both of the above methods lead to a solution of liposomes suspended in the liquid to be encapsulated which, in general, is not the ultimate objective. It is therefore necessary, afterwards, to separate the liposome vesicles from the carrier liquid and, thereafter, to redisperse them in a different aqueous phase. Such a separation of the liposomes from their initial liquid carrier can be effected for instance by chromatography on molecular sieves, on silica-gels or sephadexes (granulated polymers), or by repeated centrifugation, all methods which are tedious and not economical.

It is also possible, according to another process for the preparation of liposomes solutions, to inject an ethanol-lipid solution into the solution to be encapsulated which leads to the formation of about 25 nm liposome vesicles. However, such method is only applicable when the product to be encapsulated does not denature in the presence of alcohol and, on the other hand, the separation of the obtained vesicles from the excess of non-encapsulated liquid and their subsequent redispersion into another aqueous carrier is plagued with the same drawbacks as those mentioned above.

One has also used a method which consists in mixing a lipid and a detergent with the liquid to encapsulate and emulsifying the mixture; then, afterwards, the detergent is eliminated by dialysis. Thus, here again one obtains the liposomes dispersed in the excess of the liquid to be encapsulated from which they must be separated and purified.

It will be further remarked that the prior processes described hitherto all require to have available a volume of the starting aqueous liquid much larger than the quantity thereof which is ultimately encapsulated within the liposomes. Effectively, as explained above, in these processes the liposomes are formed as hollow beads in solution or colloidal suspension in a liquid carrier which is constituted by the portion of the original liquid to be encapsulated which has not been retained within said beads. The ratio of the liposomes encapsulated liquid to the total volume of liquid is, in general, in the region of 1 to 10% only. Consequently, if the liquid to be encapsulated is expensive—and this is generally the case with biologically active solutions—it becomes necessary to recover that portion of non-encapsulated liquid for further recycling. This recovery parallels the separation of the liposomes from that liquid. Then, after separation, the liquid must be freed from undesirable impurities and its concentration of active substances must be restored since separation and purification operations may require large volumes of solvents leading to unacceptable dilution of the active principles. Therefore, it is difficult and expensive to adapt the above processes of manufacture of the liposomes solutions to an industrial scale because of the very large volumes of liquids to be handled as compared with the relatively poor yield efficiency experienced.

There has been recently described a new method for the preparation of liposomes in aqueous solution (published German patent application DOS No. 2,532,317 and U.S. Pat. No. 4,089,901) which largely remedies the above-mentioned drawbacks. Following this method, the solution to be encapsulated is simply added to a solution of the surfactant in an organic solvent insoluble in water and of density below 1 and the mixture is sonicated as in the prior-art. After this step, there is obtained in the organic liquid a suspension of microscopic aqueous vesicles called hereinafter "liposomes precursors" which result form the dispersion of the solution to be encapsulated in the organic solvent, which vesicles are surrounded by a monolayer of lipid molecules each of which would be oriented as follows: the X function contacts the aqueous phase and, therefore, it is directed toward the inside of each droplet whereas the Y function is turned toward the outside thereof, i.e. it protrudes out of the shell and dips in the organic medium which still contains, in the dissolved state, an excess of the lipid.

Thereafter, the suspension of "precursors" is centrifugated in the presence of the aqueous medium in which it is desired to produce the liposomes solution. Since this aqueous medium is denser than the said organic solvent, it forms the bottom phase in the centrifugating tubes. During centrifugation, the "liposome precursors" leave the upper organic phase and, when subjected to the centrifugal force, they will penetrate into the aqueous phase. When doing so, they will get across the organic—water interphase which, of course, comprises a lipid barrier resulting from the presence of the excess of such lipid dissolved in the organic solvent. The molecules of the lipid in this interphase will have naturally oriented themselves according to the relative positions of the two phases, i.e. the X functions being wetted by the water and the Y function being wetted by the solvent. Hence, when crossing the barrier, the "precursors" will acquire a second layer of the surfactant, the molecules of which will be upturned relative to that of the first layer, the two layers thus constituting a normal liposome lamella of structure XY—YX. Therefore, the method directly affords the liposome solution in the desired aqueous medium.

Thus, in other words, this recent process comprises two phases: in the first phase, one forms under the effect of sonication a dispersion of vesicles or globules of the liquid to be encapsulated in another liquid insoluble or nearly insoluble in water (such globules having colloidal dimensions, i.e. 20 to 100 nm). These globules are delineated by a monomolecular pellicle of the compound XY the hydrophilic moiety X of which is turned towards the inside of the globules which contain the encapsulated liquid and the hydrophobic moiety Y of which is, contrariwise, turned toward the outside of the globules, which outside comprises the non-aqueous phase. These globules, although they are not true liposomes since they are not limited by a double molecular layer of the XY compound, can still be considered as the skeleton of the liposomes because each of them contains the same volume of the aqueous liquid that will be contained in the ultimately formed liposomes. It is therefore justified to call such globules under the name of "liposomes precursors".

By properly adjusting the respective proportions of the aqueous liquid to be encapsulated, the organic solvent and the compound of formula XY, it is possible to encapsulate within said liposome precursors the near totality of the initial aqueous liquid. The yield of the complete method is therefore often close to theory, e.g. around 80%, which constitutes a considerable improvement over the classical methods in which the yields are in the range of 1 to 20%.

The second phase of the reference process comprises forming the liposomes themselves. It can be theorized that this formation is connected with the crossing by the precursors of the monomolecular layer of the compound XY at the interphase between the non-aqueous upper-layer and the aqueous under-layer. It should be noted that the existence of such monomolecular pellicle is known per se since it intrinsically results from the properties of the surfactant XY of which the hydrophilic groups X are attracted by water whereas the lipophilic Y groups remain in contact with the organic phase. Therefore, when moving across the boundary layer, each precursor will entrain a portion of this pellicle which will tie up with the first monomolecular film surrounding the precursor and thus form the characteristic head-to-head bimolecular lamellae of the liposomes.

This method is therefore convenient as it avoids the normal operations of recovery and replenishment of the concentration in active ingredients of the initial aqueous liquid which are, as mentioned heretofore, necessary when carrying out the classical methods for the preparation of liposomes solutions. It will be also readily understandable that the reference method enables the encapsulation in liposome form of very small quantities of liquids, e.g. 0,05 to 0,1 ml, which volumes would be insufficient in case of applying the older processes. Thus, this recent reference method, which enables the direct preparation of liposomes solutions with no need to first separate the liposomes from the remainder of the initial aqueous liquid and, thereafter, to redisperse these liposomes into another desired aqueous medium, can be used in many applications in which the classical methods would not be suitable, such as biological and medical work and analyses.

It should however be remarked that, despite its strong advantages, this last method still has two drawbacks: first, the organic water-insoluble solvent must necessarily be lighter than water (to ensure the ready formation of an aqueous under-layer in the centrifugation tubes), which imposes specific solvent choice limitations. Second, the centrifugation operation is, in itself, undesirable because common high-speed centrifuges do not permit treating large quantities of liquids in one operation. Therefore, centrifugation is time consuming and expensive. Further, some sensitive biological products poorly stand the enormous accelerations (of about $10^3$ to $10^5$ g) involved in ultra-centrifugation.

The present invention fully remedies these drawbacks. Thus, the process of the invention involves, as in the above-described prior art, forming "liposome precursors", and contacting said "precursors" with an aqueous medium in a manner such that a liposome solution or suspension in said aqueous medium is produced, said "liposome precursors" consisting of small vesicles of a first aqueous phase surrounded by an envelope of a lipid or surfactant of formula XY wherein X is a hydrophilic lipophobic group and Y is lipophilic hydrophobic group, said "liposome precursors" being produced by dispersing said first aqueous phase in a water-insoluble or hardly insoluble solvent in the presence of an amount of compound XY. The process of the invention comprises emulsifying the "liposome precursors" in said aqueous medium in the presence of an excess of compound XY or another surfactant ZW wherein Z is a hydrophilic group and W is a hydrophobic group, said water insoluble or hardly soluble solvent being removed prior to or after said emulsifying.

For dispersing the first aqueous phase in the water-insoluble solvent, classical means such as sonication, violent mixing, homogenization, gas blowing, spraying, etc. can be used. Sonication is preferred for convenience. When separating the water-insoluble solvent prior to emulsifying, classical methods such as distillation, evaporation and centrifugation can be used. However, such removal of the solvent prior to emulsification can lead to undesirable partial agglomeration of the "precursors"; therefore, it is preferred to proceed with said removal of the solvent after emulsification of the "precursors" containing solvent in said aqueous medium. Said removal can be effected for instance by selective distillation or evaporation. A preferred method comprises emulsifying the two phases together and subjecting said emulsion to evaporation conditions which cause the non aqueous solvent to evaporate thus providing a solvent-free solution or suspension of liposomes in said aqueous medium.

To practically implement the operational factors of this embodiment of the invention, one can introduce a non water-soluble organic solvent into a reactor, add a lipid or a mixture of products of formula XY constituting a lipidic fraction, then add the aqueous solution to be encapsulated, homogenize the mixture and, by sonication with sonic or ultrasonic vibrations, form therein the vesicles or beads of trapped aqueous liquid called "liposome precursors". Then, one adds the desired portion of aqueous medium e.g. a diluted solution of one or several salts dissolved in water, or more simply pure water, and if necessary a further portion of compound XY or another ZW as defined above, and one subjects the mixture to the action of a stirrer-emulsifier until a homogeneous emulsion is formed. This emulsion comprises micro-drops of solvent dispersed in the aqueous phase and each micro-drop of solvent contains, dissolved, an excess of the lipid fraction and, in suspension, a variable number of liposome precursors. Then, while maintaining the emulsion in a stable condition by stirring (or even after having stopped the stirrer if the emulsion is intrinsically stable), one subjects the content of the reactor to evaporative conditions. For instance, at room pressure, one can blow air (or another gas) at the surface of the liquid (or tangentially thereto), one collects the air loaded with the solvent vapors and one circulates this air into a condenser cooled to a low temperature which effects condensation of the vapors. During evaporation and because of the consecutive size reduction undergone by the solvent drops, the liposome precursors are progressively driven off said drops and dispersed through the solvent-water boundary film therebetween and, consequently, through the lipid membrane separating the phases, thus acquiring the complementary lipid layer which converts them from the "precursor" state to the true liposome state. The resulting aqueous liposome solution therefore contains the vesicles in the dissolved or dispersed form in the said added aqueous medium. It may be advantageous to use in the last phase of the method a lipid or surfactant ZW different from XY, particularly in the case where the mutual affinity of the hydrophobic-lipophilic moieties Y and Z toward each other is greater than the affinity between two Y groups together or two W groups together. In such case (for instance when having XY being rather a good lipophilic dispersing agent and ZW being a rather good hydrophilic dispersing agent) liposomes having a shell of

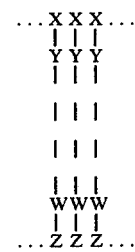

structure are obtained which are particularly stable.

This method, the yield of which is very high (about 50 to 80%), is therefore extremely simple to carry out compared to the prior-art methods. Large quantities of material can be worked up at one time and, if wanted, solvents heavier than water can be used. Solvent selection is therefore wider than in the case of the method of DOS No. 2,532,317 thus making it possible to use a great variety of surfactants including, for example, some lipids which are solids at room temperature and which, normally, had to be heated and melted, when used in connection with the older methods, at temperatures often detrimental to the products to be encapsulated. Further, this greatest choice of solvents facilitates a proper selection thereof when solvents must be found which are inert toward the active ingredients to be encapsulated.

It should be remarked that means other than those described above can be used for preparing the above emulsion and for subsequently evaporating the solvent. For instance, one can emulsify by a shaking treatment and evaporate under reduced pressure. However whatever method, the partial vapor pressure of the solvent should be significantly larger than that of water; otherwise, to prevent water exhaustion repeated water replenishment during evaporation will be required.

As solvents, one can use hydrocarbons such as benzene, toluene, cyclohexane, petroleum ether, octane, etc . . . , ethers such as diethyl-, di-isopropyl- and dibutyl-ether, etc . . . , esters such as ethyl, propyl or butyl-acetate, ethyl carbonate, etc . . . , halogenated solvents, e.g. $CCl_4$, $CHCl_2$, chloroform, benzyl chloride, etc . . .

As surfactants of formula XY or ZW, one can use, for instance, ternary or complex lipids, glycerides, cerides, etholides and sterids an, namely, one or several compounds in which the hydrophilic X respectively Z group is selected from the following phosphato, carboxyl, sulfato, amino, hydroxyl and choline and the hydrophobic Y respectively W group is one of the following: aliphatic saturated or unsaturated groups (e.g. alkyl or alkylene), polyoxyalkylene and aliphatic hydrocarbon groups substituted by at least one aromatic or cycloaliphatic rest.

It will be noted that when using XY or ZW compounds with acidic hydrophilic groups (phosphato, sulfato, etc . . . ) the obtained liposomes will be anionic (called (−) liposomes); with basic groups such as amino, cationic (+) liposomes will be obtained and with polyethyleneoxy or glycol groups, neutral liposomes will be obtained. One can find many compounds suitable for the invention in the following references: Mc Cutcheon's Detergents & Emulsifiers and Mc Cutcheon's Functional Materials, Allured Publ. Company, Ridgewood, N.J. USA. Preferably, one uses, as compounds XY or ZW, substances related to phospholipids, namely the following compounds: lecithin, phosphatidyl-ethanolamine, lysolecithin, lysophosphatidyl-ethanolamine, phosphatidylserine, phosphatidyl-inositor, sphingomyeline, cephaline, cadiolipine, phosphatidic acid, cerebrosides, dicetyl phosphate, phosphatidyl-choline and dipalmitoyl-phosphatidylcholine. As lipids with no phosphorus, one can use, for instance, stearylamine, dodecylamine, hexadecylamine (Kodak Ltd.), cetyl palmitate, glyceryl ricinoleate, hexadecyl stearate, isopropyl myristate, amphoteric acrylic polymers, triethanolamine—lauryl sulfate, alcoyl-aryl sulfonates, polyethoxylated fatty acid amides, etc . . . The lipid fraction can further contain, dissolved therein, other substances for controlling the stability and the permeability of the liposome membrane. As such, the followings can be mentioned: Sterols, e.g. cholesterol, tocopherol, phytosterols, and lanolin extracts, etc . . .

In the present process, one can encapsulate practically all hydrosoluble substances which do not have a too strong affinity for the compounds of the liposome shells or which would permeate such shells. In this respect, one can recite, besides the products already mentioned hereinbefore, aqueous solutions of biologically active substances, e.g. heavy metal chelating agents, enzymes, drugs, antibiotics, etc . . . Examples of suitable substances are listed in the following reference: "Targetting of Drugs", G. Gregoriadis, Nature 265, [2] (1967), 407.

As aqueous dispersing medium in which the liposomes are ultimately dissolved, one can use pure water or any other convenient aqueous liquid. Preferably, one uses a liquid which is intended to be the final dispersing medium for the liposomes when used, e.g. a diluted NaCl solution. In particular, one can use an aqueous NaCl solution having 0.15 mole of NaCl/liter (0.9% by weight) called physiological serum in order to directly obtain, in the course of the second step of the method, a liposome solution in a medium which can be directly injected into the body. Thus, another advantage of the present process becomes apparent: the possibility of directly obtaining a liposome suspension in a medium selected according to the end-uses of such liposomes.

Naturally, it is always possible to separate the liposomes prepared according to the present method from their aqueous dispersion medium, for instance, if it is desired to avoid all traces of non encapsulated active compound dissolved in said medium. Such separation can be carried out by any usual means, e.g. by sephadex chromatography.

The following Examples illustrate the invention in a more detailed manner.

EXAMPLE 1

In a 10 ml pyrex flask were introduced 2 ml of dibutyl ether and 1 ml of cyclohexane, then there was added 0.2 ml of a 10 mg/l insulin solution in aqueous 9°/$_{oo}$ NaCl at pH 3 (HCl N/10). Then, there was added 150 mg of dipalmitoyl-phosphatidyl-choline (hydrophilic-lipophilic compound) and, at room temperature, the heterogeneous mixture was subjected to ultra-sonics for 1 min. by means of a "BRANSON" generator (Model B-12, 20 KHz, 150 W). There was obtained a clear solution containing the liposome precursors in the form of microvesicles of the insulin solution the walls of which were made of a layer of surfactant and having molecules oriented in such direction that the hydrophilic function thereof (phosphatidylcholine) was pointing toward the inside of the vesicles and that the hydrophobic groups (hydrocarbon chains) were turned outwards towards the organic solvent. Such microvesicles were suspended in colloidal form within the organic solvent containing, dissolved, an excess of the surfactant.

Then, the organic solution was introduced into another flask containing 30 ml of neutral aqueous NaCl at 0.9% and the mixture was emulsified at 30° C. by means of an emulsifying stirrer rotating at high speed. After this step, the mixture would consist, consequently, of a dispersion of fine droplets of the organic solvent in the water phase. Each droplets would contain, in suspension, the liposome percursors described above and an excess of lipids.

By means of an appropriate tube, a current of air was introduced into the flask and made to sweep on the emulsion very close to its surface while stirring at 30° C.; the mixture of air and solvent vapors was cooled in a condenser at −10° C. whereby the vapors condensed into liquid. This operation was continued until condensation had ceased (about 20–30 min).

After this step, there remained in the flask about 20 ml of clear solution (9°/$_{oo}$ NaCl) in which the liposomes capsules were suspended in the form of vesicles the shell of which consisted of a double molecular layer of surfactant with molecules oriented head-to-head and the tails of which were directed toward the inside as well as toward the outside thereof; the external layer of this shell was acquired from the excess of lipid dissolved in the organic solvent and made available by evaporation.

Two ml of the liposome solution were chromatographed on a column containing 2.5 g of Sephadex G-50 (eluant: 0.15 M aqueous NaCl+0.05 M phosphate buffer, pH 7.5) and, by analysis of the eluate (spectrometric), it was measured that only 20–25% of the original insuline solution did escape encapsulation. Therefore, in most cases, the liposome solution obtained according to this Example can be therepeutically used as prepared without further purification.

EXAMPLE 2

An aqueous 10 g/l amyloglucosidase solution was encapsulated and dispersed into 0.15 M NaCl solution as follows: a mixture of lecithin (74 mg), 0.1 ml of the amyloglucosidase solution and diisopropyl ether (3 ml) were sonicated for 2 min (20 kHz, 150 W) while cooling below 30° C. by means of a cooling bath. There was obtained a clear homogeneous bluish liquid to which there was added 15 ml of 0.15 M aqueous NaCl. The mixture was emulsified as described in Example 1, after which the fine emulsion was swept with a current of nitrogen which evaporated the organic solvent. This blowing was continued until completion of the evaporation (20–30 min). There was obtained a clear suspension of colloidal liposomes—in which the amyloglucosidase solution was trapped—in aqueous 0.15 M NaCl and containing a very small amount (about 5%) of untrapped enzyme.

Depending on the desired use, this solution can be used as such or after the non encapsulated amyloglucosidase has been separated (e.g. by gel chromatography on "sepharose").

EXAMPLE 3

The process of Example 1 was repeated but using, as the solution to be encapsulated, 0.05 ml of an aqueous buffered solution (phosphate buffer 10 mM, pH 7.2) of 0.5 mg/ml of arabinose citosine. The dispersing phase was 0.15 M NaCl (10 ml), the lipid was cardiolipin (47 mg) and the organic solvent dibutyl ether (2.4 ml) and $CHCl_3$ (0.6 ml).

EXAMPLE 4

The process of Example 1 was repeated but using the following products: penicillamine to be encapsulated at 100 mg/ml (0.1 ml); dispersing medium 0.15 M aqueous NaCl; surfactants lecithin (105 mg) and cholesterol (35 mg); solvent butyl acetate (3 ml).

EXAMPLE 5

The process of Example 1 was repeated but using the following ingredients: to be encapsulated, betamethasone at 150 mg/l in aqueous disodium phosphate (0.05 ml); dispersing phase 0.15 M aqueous NaCl; lipid lecithin (85 mg) and phosphatidyl-ethanolamine (45 mg); solvent 3-heptanone (3 ml).

EXAMPLE 6

The method of Example 1 was repeated using as the ingredients 0.1 ml of aqueous solution of the acid complex polyinosinic-polycytidilic acids (poly(I)-poly(C)) at 1 mg/ml to be encapsulated; dispersing phase 0.15 M NaCl; surfactant lecithin (60 mg), stearylamine (20 mg) and cholesterol (15 mg); solvent a 1:1 by volume mixture of diisopropyl ether and butyl acetate (3 ml).

EXAMPLE 7

To 20 ml of diisopropyl ether were added 1.5 g of lecithin, 0.4 g of phosphatidylserine and 0.5 g of cholesterol, then a solution of 1.8 mg of actinomycin D in 3 ml of phosphate buffer (0.1 M, pH 7). The mixture was sonicated for 5 min as described in Example 1. Then there was added 100 ml of aqueous phosphate buffer (0.1 M, pH 7) and emulsification was carried out as in Example 1. Without stopping the emulsifying stirrer, the flask was connected to a vacuum tap and the pressure was progressively reduced to 10 Torr while controlling the temperature to 20°-22° C. After about 45 min, the diisopropyl ether was completely removed and the residual mixture was in the form of a clear liposome solution. By chromatography of a sample on Sephadex, it was measured that 88% of the original actinomycin D had been entrapped.

EXAMPLE 8

1 g of trypsin in 30 ml of a 0.1 M (pH 7) phosphate buffer was sonicated in the presence of a solution of 30 g of phosphatidylinositol in 100 ml of dipropyl ether. Then 460 ml of aqueous 0.5% NaCl were added and emulsification was carried out. The fine emulsion was evaporated for 3 hrs at 15° C. under 10 Torr which gave a clear liposome solution. By analysis of a sample (chromatography on Sephadex G-50) it was ascertained that the encapsulation yield was about 85%.

EXAMPLE 9

In this Example, there is described the formation of Liposomes having an asymmetrical envelope. This envelope has an inside phospholipid layer consisting of dipalmitoyl-phosphatidyl choline and an outside layer consisting of a mixture of egg-lecithin and phosphatidylserine. The following method was used:

To 3 ml of dibutyl-ether, there were added 0.1 ml of an aqueous solution at 0.001 M of 3,9-bisdimethylaminophenazothionium chloride and at 0.015 M of NaCl and 55 mg of dipalmitoylphosphatidylcholine; then the mixture was sonicated as described in Example 1 and there was obtained a transparent organic solution containing microvesicles (liposomes precursors) of the above mentioned colored aqueous solution surrounded by a layer of dipalmitoyl-phosphatidylcholine. This organic solution was thereafter centrifugated for 20 min. at 8000 g. After the end of this operation, there was obtained a clear supernatant phase and a translucent blue bottom phase containing the microvesicles agglomerated together under the effect of the centrifugal force. This phase which was in the form of a rather consistent gel was transformed into a 10 ml container, there it was mixed, by means of a spatula, with 0.3 ml of a 200 mg/ml solution of a 20:1 (mole ratio) mixture of egg-lecithin and phosphatidylserine in dibutylether. Then there was added to the gummy mass 5 ml of a 0.15 M NaCl water solution and the mixture was subjected to vigourous agitation with a magnetic stirrer. The mass progressively dispersed itself and, after 10–15 min, there was obtained a well homogeneous, transparent solution containing, in suspension, the liposomes with a mixed envelope. The outside layer of this envelope consisted of the mixture of egg-lecithin and phosphatidylserine and the inside layer thereof consisted of dipalmitoyl-phosphatidylcholine.

EXAMPLE 10

Liposomes precursors containing insulin were prepared as described in Example 1. Then, instead of continuing as further described in Example 1, i.e. directly emulsifying the organic solution containing the microvesicles in an aqueous 0.9% NaCl solution, the organic solution was first concentrated by subjecting to reduced pressure (20 Torr) at room temperature. After evaporation of the organic solvents, there was obtained at the bottom of the container an oily translucent layer consisting of agglomerated microvesicles. There were then added in the flask 7 ml of an aqueous 0.9% NaCl solution and, by means of a magnetic stirrer, this oily phase was dispersed into the aqueous medium. This oily phase progressively disappeared and, after 10-15 min, there was obtained a transparent homogeneous solution containing, in suspension, the desired liposomes. After chromatographing this solution on "Sephadex 4B" (Pharmacia, Sweden), analysis of the non encapsulated phase showed that 52% of the starting insulin had been effectively encapsulated in the liposomes.

EXAMPLE 11

A mixture of lecithin (40 g), dibutylether (600 ml) and an aqueous 0.9% NaCl solution containing 10 g/l of insulin (400 ml) were homogenized by means of a MINISONIC homogenizer (ULTRASONICS Ltd., Great-Britain). There was obtained a stable milky-looking solution which was introduced into a 4 l flask containing 2 l of an aqueous 0.9% NaCl solution; then, by means of an emulsification stirrer, the organic suspension and the aqueous medium were emusified together (15 min). Thereafter the organic solvent was removed by air-stripping, i.e. the mixture was circulated downwards a column traversed by an ascending air current, the latter being collected, when loaded with the solvent vapors, at the top of the column; there was thus obtained a homogeneous translucent solution of liposomes containing the insulin.

EXAMPLE 12

Dibutylether (3 ml), aqueous 9°/₀₀ NaCl containing 10 mg/ml of insulin (1 ml) and lecithin (125 mg) were introduced in a strong 10 ml Pyrex tube, together with 2 g of 1 mm diameter glass beads. The tube was stoppered, was placed on a shaker and shaked for 30 min at 100 cycles per min. There was thus obtained a rather homogeneous milky-looking solution which was poured into a 100 ml flask containing aqueous 9°/₀₀ NaCl (30 ml). Then, the organic solvent was evaporated as described in Example 2 by using a current of nitrogen. After sweeping for 20-30 min, there was obtained a limpid solution of liposomes containing the insulin under encapsulated form.

I claim:

1. In a process for the preparation of a solution or suspension of liposomes in an aqueous medium in which a non-aqueous dispersion of liposome precursors is first produced by dispersing a first aqueous liquid in an essentially water-insoluble solvent in the presence of a compound of the formula XY wherein X is a hydrophilic lipophobic group and Y is a lipophilic hyrophobic group, said liposome precursors consisting of small vesicles of the first aqueous liquid surrounded by a monomolecular film of compound XY, the improvement comprising thereafter emulsifying the liposome precursors in said aqueous medium in the presence of a compound of the formula ZW wherein Z is a hydophilic group and W is a hydophobic group to thereby form a solution or suspension of liposomes consisting of the first aqueous liquid surrounded by a bimolecular film of structure XY-WZ, and water-insoluble solvent being removed prior to or after said emulsification.

2. The process of claim 1 wherein the compound ZW is compound XY thereby forming a bimolecular film of the structure XY-YX.

3. The process of claim 1 in which the dispersion of the liposome precursors is emulsified in said aqueous medium and the solvent is thereafter removed by evaporation.

4. A process for the preparation of a solution or suspension of liposomes in an aqueous medium comprising the steps of dispersing a first aqueous liquid in an essentially water-insoluble solvent in the presence of a compound of the formula XY wherein X is a hydrophilic lipophobic group and Y is a lipophilic hydrophobic group to form a dispersion of liposome precursors in the solvent, the precursors consisting of small vesicles of the first aqueous liquid surrounded by a monomolecular film of compound XY, emulsifying the liposome precursors in a second aqueous medium in the presence of a compound of the formula ZW wherein Z is a hydrophilic group and W is a hydrophobic group to thereby form a solution or suspension of liposomes in the second aqueous medium, said liposomes consisting of the first aqueous liquid surrounded by a bimolecular film of the structure XY-WZ and removing the water-insoluble solvent prior to or after said emulsification.

5. The process of claim 4, wherein the dispersion of said first liquid in the water-insoluble solvent is carried out with the aid of sonic or ultra-sonic vibration.

6. The process of claim 4 in which the compound ZW is compound XY thereby forming a bimolecular film of structure XY-YX.

7. The process of claim 4 in which the dispersion of liposome precursors is emulsified in the second aqueous medium and the solvent is removed after by evaporation.

8. A process for the preparation of a solution or suspension of liposomes in an aqueous medium comprising the steps of dispersing a liquid product to be encapsulated with the aid of sonic or ultrasonic vibration in an essentially water-insoluble solvent containing in solution an excess of a compound of the formula XY wherein X is a hydrophilic lipophobic group and Y is a hydrophobic lipophilic group to form a dispersion of liposome precursers in the solvent consisting of vesicles of the liquid product surrounded by a monomolecular film of the compound XY, emulsifying this dispersion of liposome precursors containing an excess of the XY compound in a second aqueous medium to form a solution or suspension of liposomes consisting of vesicles of the liquid product surrounded by a bimolecular film of structure XY-YX and thereafter removing the solvent by evaporation to provide a solvent-free solution or suspension of the liposomes in said aqueous medium.

9. The process of claim 4 or 8 wherein compound XY is a lipid selected from the group consisting of lecithin, phosphatidyl-ethanolamine, lysolecithin, lysophosphatidylethanolamine, phosphatidylserine, phosphatidylinositol, sphingomyelin, cardiolipin, phosphatidic acid, cerebrosides, stearylamine and dipalmitoylphosphatidylcholine.

10. The process of claim 4 or 8 in which the compound of formula XY is a mixture of at least one phospholipid and at least one other lipid belonging to a category of lipids other than phospholipids.

11. The process of claim 10 in which the other lipid is selected from the group consisting of cholesterol and tocopherol.

12. The process of claim 4 in which the compound ZW is a mixture of at least one phospholipid and at least one other lipid belonging to a category of lipids other than phospholipids.

13. The process of claim 12 wherein said other lipid is selected from the group consisting of cholesterol and tocopherol.

14. The process of claim 4 or 8 wherein the water-insoluble solvent is selected from the group consisting of benzene, alkyl-benzene haloalkylbenzene, aliphatic ethers, aldehydes, esters and ketones and free and halogenated aliphatic and cycloaliphatic hydrocarbons.

15. The process of claim 8 wherein the liquid product to be encapsulated is selected from the group consisting of dyestuffs, flavors, fragrances, antibiotics, enzymes, polypeptides and chelating agents.

16. The process of claim 4 or 8 wherein the second aqueous medium is pure water or an aqueous solution of a water-soluble salt.

17. The process of claim 16 wherein the aqueous medium is 0.15 M NaCl aqueous solution.

18. The process of claim 8 wherein said evaporation of the solvent is provided by sweeping a gas over the aqueous medium.

19. The process of claim 8 wherein evaporation is provided by the application of reduced pressure.

* * * * *